(12) United States Patent
Whiteley

(10) Patent No.: US 6,496,252 B1
(45) Date of Patent: Dec. 17, 2002

(54) DIFFERENTIAL-TILT RYTOV PARAMETER MONITOR FOR ATMOSPHERIC TURBULENCE

(75) Inventor: Matthew R. Whiteley, Albuquerque, NM (US)

(73) Assignee: The United States of America as represented by the Secretary of the Air Force, Washington, DC (US)

(*) Notice: Subject to any disclaimer, the term of this patent is extended or adjusted under 35 U.S.C. 154(b) by 0 days.

(21) Appl. No.: 09/579,993

(22) Filed: May 26, 2000

(51) Int. Cl.[7] .................................................. G01J 1/00
(52) U.S. Cl. ......................................... 356/121; 73/147
(58) Field of Search ............................ 356/121, 122, 356/141.3, 128; 250/201.9; 73/147, 861.06

(56) References Cited

U.S. PATENT DOCUMENTS

| | | | |
|---|---|---|---|
| 5,150,171 A | 9/1992 | Hill | 356/128 |
| 5,303,024 A | 4/1994 | Thierman | 356/128 |
| 5,343,287 A | 8/1994 | Wilkins | 356/141.3 |
| 5,796,105 A | 8/1998 | Wang | 250/338.5 |

OTHER PUBLICATIONS

D. L. Fried, "Optical resolution through a randomly inhomogeneous medium for very long and very short exposures," *J. Opt. Soc. Am.* 56, pp. 1372–1379, Oct. 1996.
D. L. Fried, "Branch point problem in adaptive optics," *J. Opt. Sci. Am.* A 15, pp. 2759–2768, Oct. 1998.
D. L. Fried, "Differential angle of arrival: Theory, evaluation, and measuremet feasibility," *Radio Science* 10, pp. 71–76, Jan. 1975.

F. D. Eaton, et al., "Comparison of two techniques for determining atmospheric seeing," in *Proc. SPIE: Optical, Infrared, and Millimeter Wave Propagation Engineering*, vol. 926, pp. 319–334, 1988.

F. D. Eaton, et al., "Phase structure function measurements with multiple apertures," in *Proc. SPIE: Propagation Engineering*, vol. 1115, pp. 218–223, 1989.

M. R. Whiteley, "Rytov parameter estimation by use of differential–tilt measurements," to be published.

M. R. Whiteley, *Optimal atmospheric compensation for anisoplanatism in adaptive–optical systems*, Ph.D. thesis, Air Force Institute of Technology, Wright–Patterson AFB, Ohio, 1998.

*Primary Examiner*—Frank G. Font
*Assistant Examiner*—Layla Lauchman
(74) *Attorney, Agent, or Firm*—James M. Skorich; Kenneth E. Callahan

(57) ABSTRACT

An optical configuration and related analysis techniques are presented that provide a practical method for determining the Rytov parameter based on the difference of variances for the differential image motion (average wavefront gradient or wavefront tilt) between two receiving apertures. The Rytov parameter is the log-amplitude variance predicted by an approximate solution to Maxwell's equations for propagation through media with random index of refraction (Rytov theory). It is a useful metric of the optical effects for extended turbulence propagation and is a leading indicator of the performance limitations of adaptive optical compensation devices not related to the transverse coherence diameter. A time-duplex alternative apparatus and a single source alternative apparatus are also disclosed.

4 Claims, 12 Drawing Sheets

DIFFERENTIAL-TILT RYTOV PARAMETER MONITOR FOR ATMOSPHERIC TURBULENCE

STATEMENT OF GOVERNMENT INTEREST

The conditions under which this invention was made are such as to entitle the Government of the United States under paragraph 1(a) of Executive Order 10096, as represented by the Secretary of the Air Force, to the entire right, title and interest therein, including foreign rights.

BACKGROUND OF THE INVENTION

1. Field of the Invention

The present invention is in the field of atmospheric turbulence, and in particular, relates to an optical apparatus designed to provide in-situ estimates of the Rytov parameter for the propagation of light through atmospheric optical turbulence.

2. Description of the Prior Art

The term "Rytov parameter" refers to the theoretical log-amplitude variance predicted by Rytov theory. The Rytov parameter for spherical-wave propagation is given as a weighted integral of the random index-of-refraction structure constant $C_n^2$ as follows:

$$\sigma_\chi^2 \equiv 0.5631 \left(\frac{2\pi}{\lambda}\right)^{7/6} \int_0^L dz C_n^2(z) [z(1-z/L)]^{5/6} \quad (1)$$

where $\lambda$ is the wavelength, L is the propagation distance, and z is a position along the propagation path. Though strictly a theoretical quantity, the Rytov parameter is a useful metric of the optical effects for extended-turbulence propagation and is a leading indicator of the performance limitations of adaptive-optical compensation devices not related to the transverse coherence diameter (Fried parameter) (D. L. Fried, "Optical resolution through a randomly inhomogeneous medium for very long and very short exposures," *J. Opt. Soc. Am.* 56, pp. 1372–1379, October 1966). This instrument bases the estimate of the Rytov parameter on an appropriate difference of variances for the differential image motion (average wave-front gradient, wave-front tilt) between two receiving apertures. The use of differential tilts for determining the Rytov parameter is a primary novel aspect of this invention, for these quantities are not conventionally recognized to be indicative of the Rytov parameter. When interpreted properly, differential-tilt measurements are a reliable and predictable indicator of the Rytov parameter. It is important to clarify that the differential-tilt Rytov parameter monitor is used to estimate the value of the integral expression for $\sigma_\chi^2$ given in Eq. (1), not the observed log-amplitude variance for point-source propagation.

The Rytov approximation is the predominant theoretical construct used to derive a solution to the scalar wave equation for propagation through a medium with random index-of-refraction fluctuations. Analysis of turbulence effects using the Rytov approximation is often referred to as "Rytov theory." The variance of the log-amplitude computed using Rytov theory is called the "Rytov parameter." This quantity is designated $\sigma_\chi^2$ is related to point source propagation parameters as indicated in Eq. (1). While Eq. (1) indicates that $\sigma_\chi^2$ should increase proportionately with any constant multiplier of $C_n^2$, experimental and simulation-based studies have concluded that this trend does not hold for full-wave propagation. Instead, the irradiance variance (scintillation) increases monotonically from 0 to a maximum value greater than 1, then decreases as $C_n^2$ increases. This behavior is referred to as the "saturation" of scintillation. Saturation imposes a limit on the utility of irradiance-based instrumentation (scintillometers) to adz accurately determine turbulence strength parameters using Rytov theory. In many experiments, the Rytov parameter cannot be measured directly, but rather must be inferred from measurable quantities making key assumptions about the turbulence profile that are not generally valid.

The Rytov parameter is often used to quantify the severity of turbulence effects in propagation, especially in studies of scintillation. Moreover, the Rytov parameter is a critical metric in determining the utility of adaptive-optical systems for compensation of extended-turbulence effects. Recently, it has been recognized that the Rytov parameter is related to a rotational component of the turbulence-induced phase due to phase dislocations (branch points) which limit the ability of conventional wave-front reconstruction procedures (D. L. Fried, "Branch point problem in adaptive optics," *J. Opt. Soc. Am. A* 15, pp. 2759–2768, October 1998). The Rytov parameter addresses additional adaptive optics performance degradation not quantified by considering only the transverse atmospheric coherence length $r_0$ or Fried parameter. Thus, it is desirable to accurately estimate the Rytov parameter in field experiments where little or nothing is known about $C_n^2(z)$. For simulation studies, the Rytov parameter may be computed directly from the input parameters. An accurate estimate of the Rytov parameter in practical experiments therefore facilitates comparison with simulation-based studies.

In current laser propagation and adaptive-optical compensation field tests, at least two types of atmospheric characterization measurements are typically made. The first type of measurement relates to the variation of the received irradiance or scintillation. This measurement is made with a device called a scintillometer, which measures the random fluctuation of received light in a collection aperture. Devices of this type have been patented by Hill and Ochs (U.S. Pat. No. 5,150,171, Thierman (U.S. Pat. No. 5,303,024), and Wang (U.S. Pat. No. 5,796,105). For conventional scintillometers, the irradiance variance is computed from the data and analysis is performed to yield an estimate of $C_n^2$. Since these measurements are typically made over nearly horizontal paths, it is assumed that $C_n^2$ varies little over the path. The observed irradiance variance may be interpreted using Rytov theory in the weak-fluctuations regime, or a comparison with wave-optics simulation results may be made in the saturated or asymptotic regimes. From the estimate of $C_n^2$ obtained with the scintillometer, the Rytov parameter may then be computed using Eq. (1).

The second type of atmospheric characterization measurement often made in field tests relates to the strength of the turbulence-induced phase, quantified by the transverse coherence length $r_0$ which is related to point-source propagation parameters as follows:

$$r_0 \equiv \left(\left[\frac{2.91}{6.88}\left(\frac{2\pi}{\lambda}\right)^2 \int_0^L dz C_n^2(z)(1-z/L)^{5/3}\right]\right)^{-3/5} \quad (2)$$

A mathematical comparison between Eq. (1) for $\sigma_\chi^2$ and Eq. (2) for $r_0$ indicates that while the bulk of the contribution to $\sigma_\chi^2$ comes from the middle of the propagation path, $r_0$ is affected primarily by turbulence near the receive aperture. Thus, $\sigma_\chi^2$ and $r_0$ are indicative of disparate optical effects arising from different regions of the propagation path. For an optical system with diameter D, atmospheric effects on resolution are determined by the quantity $(D/r_0)^{5/3}$. A device for measuring $r_0$ has been patented by Wilkins (U.S. Pat. No. 5,343,287) that employs beam-spread and angle-of-arrival variance. However, work dating back more than 20 years (D. L. Fried, "Differential angle of arrival: Theory, evaluation, and measurement feasibility," *Radio Science* 10, pp. 71–76, January 1975; F. D. Eaton, et al., "Comparison of two techniques for determining atmospheric seeing," in *Proc. SPIE: Optical, Infrared, and Millimeter Wave Propagation Engineering,* vol. 926, pp. 319–334, 1988; and F. D. Eaton, et al., "Phase structure function measurements with multiple apertures," in *Proc. SPIE: Propagation Engineering,* vol. 1115, pp. 218–223, 1989) demonstrates the superiority of techniques employing differential angle-of-arrival measurements of two spatially-separated receive apertures for estimating $r_0$.

In cases where $C_n^2$ may reasonably be assumed constant over the entire propagation path, either irradiance variance measurements from a scintillometer or $r_0$ measurements from a suitable device could be used to compute $C_n^2$ from Rytov theory or simulation, and the Rytov parameter could then be computed using Eq. (1). In practice, however, constant $C_n^2$ is rarely observed over a propagation distance greater than several hundred meters. Thus, neither the irradiance-based (scintillometer) nor conventional phase-variance-based techniques provide a reliable method for determining the Rytov parameter. Additionally, analysis of scintillometer data using wave-optics simulations may require a measurement of the inner scale of turbulence for enhanced fidelity. Taken together, limitations of the available devices and techniques for atmospheric characterization may lead to large errors in estimating the Rytov parameter for realistic turbulence profiles.

SUMMARY OF THE INVENTION

The differential-tilt Rytov parameter monitor is an optical apparatus, which when combined with related processing and data analysis techniques, provides in-situ estimates of the theoretical expression of the Rytov parameter for point source propagation of light through atmospheric optical turbulence. The Rytov parameter is the theoretical log-amplitude variance predicted by Rytov theory. It is a useful metric of the optical effects for extended turbulence propagation and is a leading indicator of the performance limitations of adaptive optical compensation devices not related to the transverse coherence diameter (Fried parameter). The present invention bases the estimate of the Rytov parameter on an appropriate difference of variances for the differential image motion (average wavefront gradient and wavefront tilt) between two receiving apertures, quantities that are not conventionally recognized to be indicative of the Rytov parameter. A time-duplex alternative apparatus and a single source alternative apparatus are also disclosed.

BRIEF DESCRIPTION OF THE DRAWINGS

The various features of novelty that characterize the invention are pointed out with particularity in the claims annexed to and forming a part of this disclosure. For a better understanding of the invention, its operating advantages, and specific objects attained by its uses, reference is made to the accompanying drawings and descriptive matter in which a preferred embodiment of the invention is illustrated.

FIG. 3(*b*) shows the normalized weighting function for the difference of differential-tilt variance $\sigma_\delta^2$.

FIG. 6(*b*) is a plot of the equivalent jitter $\sigma_\delta$ (in units of $\lambda/D$) for various system Fresnel numbers.

FIG. 9(*b*) is a plot of the relative error of the Rytov parameter estimator for the single-source alternative system.

DESCRIPTION OF THE PREFERRED EMBODIMENT

To avoid the difficulties associated with Rytov parameter estimation using conventional instruments, novel instrumentation and data processing has been developed to obtain a quantity that is proportional to the Rytov parameter by using differential-tilt measurements. This technique is referred to as the difference of differential-tilt variance (DDTV). The instrumentation and processing supporting this technique are described below. The theory of operation of this instrument is also outlined. For certain configurations of the proposed optical apparatus, the relative error in the Rytov parameter estimate is approximately 0.05. The differential-tilt technique described here is insensitive to gimbal motion, additive detector noise, turbulence outer scale, and saturation effects.

Figure 1:
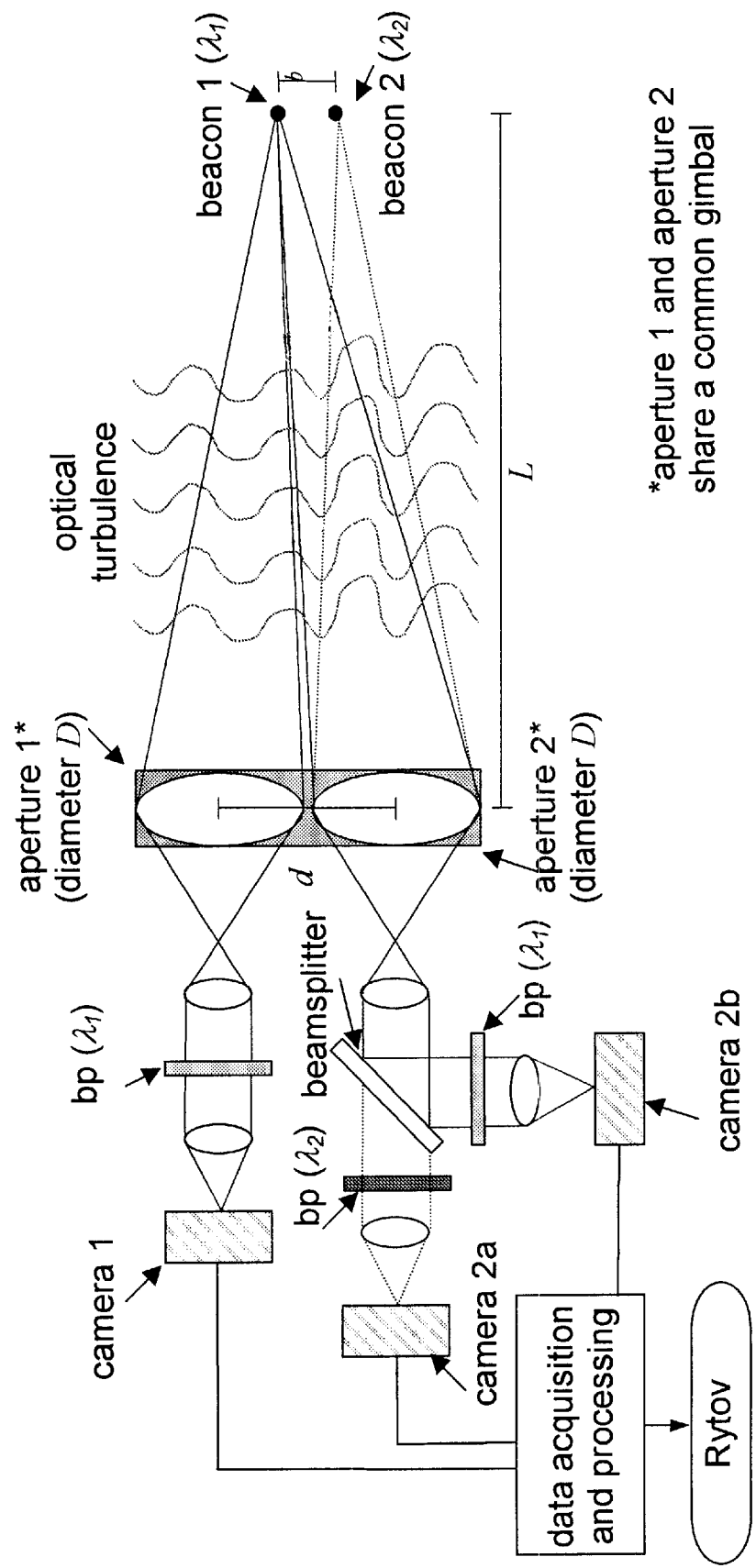
FIG. 1 is a schematic of the apparatus required for the differential-tilt Rytov parameter monitor.

The basic optical apparatus for the differential-tilt Rytov parameter monitor is shown in FIG. 1. Two point sources are located in a plane separated by a distance b. These sources, referred to as beacon 1 and beacon 2, and are of wavelength $\lambda_1$ and , $\lambda_2$ respectively. Light from these beacons propagates a distance L through atmospheric turbulence to a plane containing two clear apertures of diameter D separated by a distance d in the same direction as the beacons. These apertures are referred to as aperture 1 and aperture 2, and are mounted on the same telescope gimbal. Light entering aperture 1 is relayed through a spectral bandpass filter of center wavelength $\lambda_1$ and forms an image on the focal plane of an electronic camera designated camera 1. Light entering aperture 2 is relayed to a beam-splitter element, which divides the light into two optical legs. In one leg, the light passes through a spectral bandpass filter of center wavelength $\lambda_2$ and forms an image on the electronic camera designated camera 2*a*. In the other leg, the light passes through a spectral bandpass filter of center wavelength $\lambda_1$ and forms an image on the electronic camera designated camera 2*b*. The point source beacons should be separated in wavelength by the smallest possible amount that permits proper rejection by the bandpass filters used in the system. All processing of the camera data to obtain an estimate of the Rytov parameter is accomplished by a data acquisition computer.

At each measurement time t, images are formed in each of the three cameras. The image data are designated as $I_1(\vec{\alpha}_1, t)$, $I_{2a}(\vec{\alpha}_{2a}, t)$ and $I_{2b}(\vec{\alpha}_{2b}, t)$ for camera 1, camera 2a, and camera 2b, respectively. The angular position within the images are designated $\vec{\alpha}_1$, $\vec{\alpha}_{2a}$ and $\vec{\alpha}_{2b}$. Using the camera data, the data acquisition and processing computer calculates an angular image centroid (in units of $\lambda/D$) at each time t for each camera as follows:

$$d_1(t) = \frac{D}{\lambda_1} \frac{\sum_{x=1}^{M}\sum_{y=1}^{M} \alpha_{1x} I_1(\alpha_{1x}, \alpha_{1y}; t)}{\sum_{x=1}^{M}\sum_{y=1}^{M} I_1(\alpha_{1x}, \alpha_{1y}; t)}, \quad (3)$$

$$d_{2a}(t) = \frac{D}{\lambda_2} \frac{\sum_{x=1}^{M}\sum_{y=1}^{M} \alpha_{2ax} I_{2a}(\alpha_{2ax}, \alpha_{2ay}; t)}{\sum_{x=1}^{M}\sum_{y=1}^{M} I_{2a}(\alpha_{2ax}, \alpha_{2ay}; t)}, \quad (4)$$

$$d_{2b}(t) = \frac{D}{\lambda_1} \frac{\sum_{x=1}^{M}\sum_{y=1}^{M} \alpha_{2bx} I_{2b}(\alpha_{2bx}, \alpha_{2by}; t)}{\sum_{x=1}^{M}\sum_{y=1}^{M} I_{2b}(\alpha_{2bx}, \alpha_{2by}; t)}, \quad (5)$$

where M is the number of pixels on the side length of each camera image. The x and y coordinate axes for each image are chosen such that the x axis is in the same direction as the separation vector from beacon 1 to beacon 2. After obtaining N centroid measurements from the images of each camera, the difference of differential tilt variance (DDTV) quantity $\sigma_\delta^2$ is computed as follows:

$$\sigma_\delta^2 = \langle [d_1(t) - \langle d_1(t)\rangle - d_{2a}(t) + \langle d_{2a}(t)\rangle]^2 \rangle - \langle [d_1(t) - \langle d_1(t)\rangle - d_{2b}(t) + \langle d_{2b}(t)\rangle]^2 \rangle, \quad (6)$$

where $\langle . \rangle$ represents averaging over the ensemble of N centroid measurements obtained over a time period $\tau_N$. After computing $\sigma_\delta^2$ from the data according to Eq. (6), the Rytov parameter estimate is obtained as follows:

$$\sigma_x^2 \cong \left[ \frac{0.1242\pi^2}{128\sqrt{3}\,\Gamma(8/3)(2\pi)^{5/6} W_{0\delta}} \right] F_D^{-5/6} \sigma_\delta 2 \quad (7)$$

where $F_D = D^2/(\lambda L)$, the Fresnel number of each aperture for propagation over the range L at wavelength $\lambda$ (we assume $\lambda = \lambda_1 \cong \lambda_2$). The quantity $W_0\delta$ in Eq. (7) depends upon the relative aperture separation d/D and the relative beacon separation b/D. While a reasonable estimate of Rytov parameter may be obtained for a range of values for d/D and b/D, it has been found that the DDTV technique works well for d/D=1 and b/D=0.2. In this particular configuration, $W_{0\delta} = 3.78 \times 10^{-5}$.

Independent Rytov parameter estimates can be made at a rate inversely proportional to the period $\tau_N$. The proper ensemble period will depend upon the wind velocity v and the aperture diameter D. As a conservative guideline, $\tau_N$ should be chosen such that $v\tau_N/D = 20000$. Additionally, the exposure period $\tau_c$ for each camera image should be no larger than $v\tau_c/D = 0.01$. For v=10 m/s and D=0.1 m, $\tau_N = 200$ s and $\tau_c = 100$ μs. The number of centroid measurements N should be approximately 2000 over the period $\tau_N$. Thus, for v=10 m/s and D=0.1 m, 100 microsecond exposures should be made on each camera at a 10 Hz rate. In this case, independent Rytov estimates would be made at approximately 3-minute intervals. The update rate of the reported Rytov parameter could be made more frequently by buffering the centroid data and employing a sliding data analysis window of the appropriate size within the processing routines. For instance, by recomputing the value of $\sigma_\delta^2$ each time 100 new centroid measurements are available, the Rytov estimate could be updated every 10 seconds (for v=10 m/s and D=0.1 m).

Figure 2:
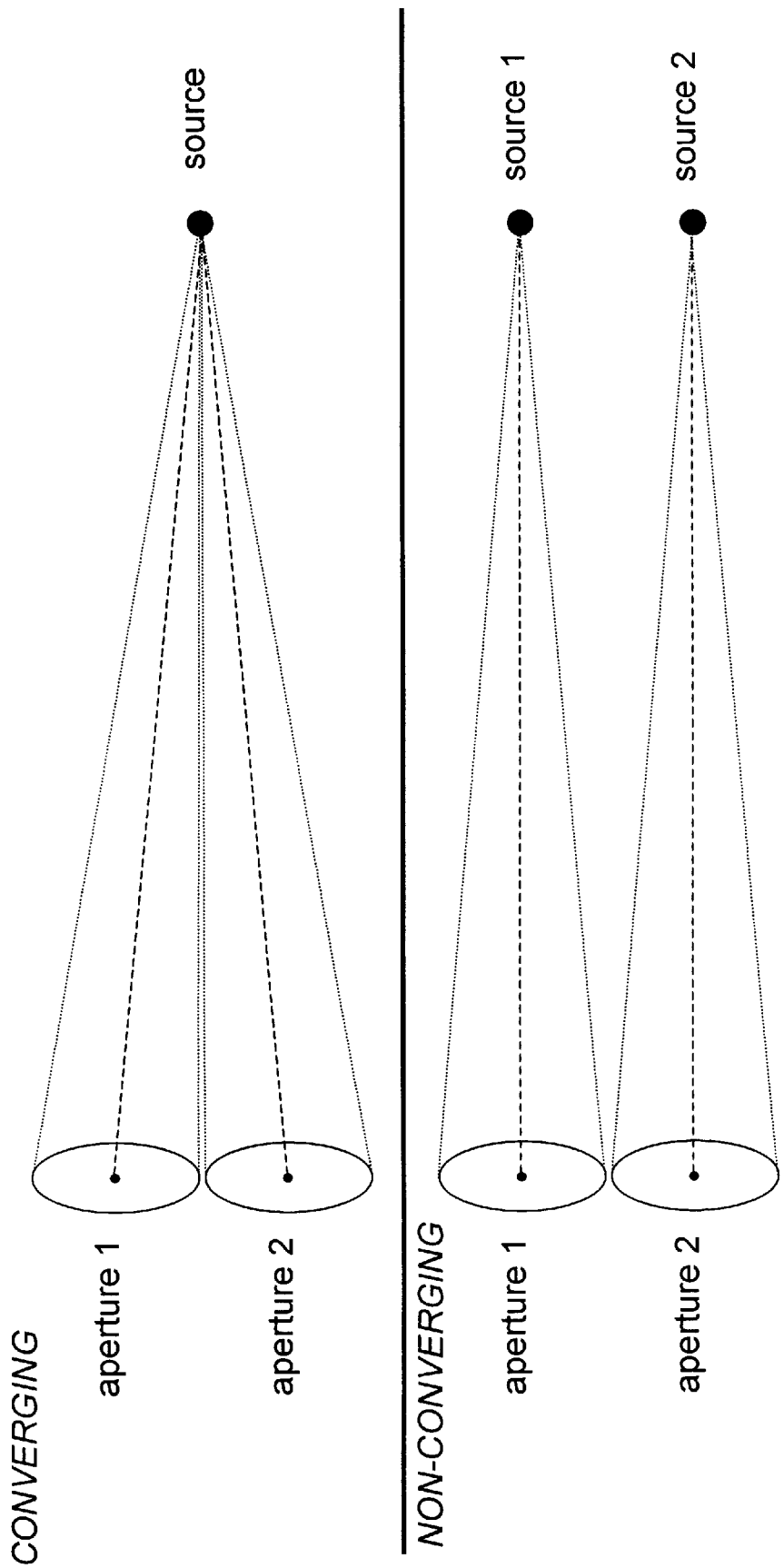
FIG. 2 is a schematic diagram of the two optical configurations (converging and non-converging) required for Rytov parameter estimation from differential-tilt measurements.

The fundamental theory of operation for the DDTV technique is described in detail in (M. R. Whiteley, "Rytov parameter estimation by use of differential-tilt measurements," to be published), and herein incorporated by reference, which builds upon fundamental calculations made in (M. R. Whiteley, *Optimal atmospheric compensation for anisoplanatism in adaptive-optical systems*, Ph.D. thesis, Air Force Institute of Technology, Wright-Patterson AFB, Ohio, 1998). The development is summarized here to justify the use of Eq. (7) in estimating the Rytov parameter. The analysis begins by considering the difference of the differential-tilt variance for the two optical configurations shown in FIG. 2. When both apertures observe a single point source, the configuration is referred to as converging. When the apertures observe separate point sources, the configuration is referred to as non-converging. Relating back to the optical apparatus shown in FIG. 1 and the prior processing description, the set of angular centroid measurements $d_1(t)$, $d_{2b}(t)$ are associated with a 'converging' geometry, whereas the set $d_1(t)$, $d_{2a}(t)$ are associated with a 'non-converging' geometry.

To derive the relationship between the Rytov parameter and $\sigma_\delta^2$ shown in Eq. (7), we first consider a measurement model for centroid data from each aperture with non-converging and converging propagation paths. In this measurement model, we express each tilt measurement as the sum three components; atmospheric, noise, and gimbal motion. Accordingly, the tilt data from each aperture is given by (implicitly at time t):

$$d_1 = t_1 + n_1\theta$$
$$d_{2a} = t_{2a} + n_{2a} + \theta$$
$$d_{2b} = t_{2b} + n_{2b} + \theta \quad (8)$$

In Eq. (8), $t_1$, $t_{2a}$, and $t_{2b}$, represent atmospheric tilt components of the measured data from each optical path. Also, $n_1$, $n_{2a}$, $n_{2b}$ represent the detector-noise-induced angle for each data channel. The contribution of gimbal motion to the measured tilt in each channel is given by $\theta$ (gimbal motion contributes the same tilt to each aperture). Each of the tilt components in Eq. (8) are zero mean, and therefore each of the tilt data signals is zero mean.

From the expression for $\sigma_\delta^2$ in Eq. (6) and the measurement model given in Eq. (8) it follows that:

$$\sigma_\delta^2 = \langle (t_1 - t_{2a} + n_1 - n_{2a})^2 \rangle - \langle (t_1 - t_{2a} + n_1 - n_{2a})^2 \rangle \quad (9)$$

$$= \langle t_1^2 \rangle + \langle t_{2a}^2 \rangle - 2\langle t_1 t_{2a}\rangle + \langle n_1^2 \rangle + \langle n_{2a}^2 \rangle - 2\langle n_1 n_{2a}\rangle -$$

$$\langle t_1^2 \rangle - \langle t_{2b}^2 \rangle + 2\langle t_1 t_{2b}\rangle - \langle n_1^2 \rangle - \langle n_{2b}^2 \rangle + \langle n_1 n_{2b}\rangle$$

$$= 2(\langle t_1 t_{2b}\rangle - \langle t_1 t_{2a}\rangle)$$

In the steps leading up to Eq. (9), the noise variances and covariances are assumed to be equal for the converging and non-converging geometries. We also assume that the noise terms are uncorrelated with the atmospheric tilts. Notice that the gimbal-motion contributions are canceled by the differencing of the tilt measurements for the common-gimbal apertures. Furthermore, the atmospheric tilt variances as well as the noise variances and covariances are canceled by the differencing of the differential-tilt variances. Thus, $\sigma_{67}^2$ is insensitive to contamination from gimbal motion and any additive noise source.

Eq. (9) gives $\sigma_\delta^2$ as twice the difference the atmospheric tilt covariance for the converging geometry and the atmospheric tilt covariance for the non-converging geometry. Analysis shows that the expression for $\sigma_\delta^2$ in Eq. (9) can be written in terms of turbulence parameters as follows:

$$\sigma_\delta^2 = \frac{128\sqrt{3}\,\Gamma(8/3)}{\pi^2}\left(\frac{2\pi}{\lambda}\right)^2 D^{5/3} L W_{0\delta} \int_0^1 d\xi\, C_n^2(\xi L) W_\delta(\xi), \quad (10)$$

where the units of $\sigma_\delta^2$ are $(\lambda/D)^2$. In Eq. (10), $w_\delta(\xi)$ is the normalized path weighting function given by:

$$w_\delta(\xi) \equiv \frac{W_\delta(\xi)}{\int_0^1 d\xi\, W_\delta(\xi)} \quad (11)$$

$$= \frac{W_c(\xi) - W_p(\xi)}{\int_0^1 d\xi\, W_c(\xi) - W_p(\xi)}$$

$$= \frac{W_c(\xi) - W_p(\xi)}{W_{0c} - W_{0p}},$$

where $W_{0c}$ and $W_{0p}$ are the integrals of $W_c(\xi)$ and $W_p(\xi)$, respectively. The functions $W_c(\xi)$ and $W_p(\xi)$, are weighting functions for the converging (c) and non-converging (p) propagation geometries, both of which are special cases of a generalized weighting function for tilt covariance, designated here as $W(\xi)$. The function $W(\xi)$ depends upon the dimensionless parameter $\beta(\xi)$:

$$\beta(\xi) = \frac{1-\xi}{2\gamma(1-\xi) + \mu\xi}, \quad (12)$$

where $\gamma$ relates to the aperture separation, and $\mu$ relates to the beacon separation. The value of $\beta(\xi)$ determines the expression for $W(\xi)$ as follows:

For $[\beta(\xi)]^2 < \frac{1}{4}$:

$$W(\xi) = 2^{-14/3}(1-\xi)^{5/3} \begin{bmatrix} 2^{-17/3}[\beta(\xi)]^{1/3}\dfrac{\Gamma(1/6)}{\Gamma(5/6)}{}_3F_2\{1/6, 1/6, 5/2; 3, 5;[2\beta(\xi)]^2\} \\ -2^{-17/3}[\beta(\xi)]^{1/3}\dfrac{\Gamma(7/6)}{\Gamma(11/6)}{}_3F_2\{-5/6, 7/6, 5/2; 3, 5;[2\beta(\xi)]^2\} \end{bmatrix} \quad (13)$$

For $[\beta(\xi)]^2 \geq \frac{1}{4}$:

$$W(\xi) = 2^{-14/3}(1-\xi)^{5/3} \quad (14)$$

$$\begin{bmatrix} \dfrac{\Gamma(1/6)\Gamma(7/3){}_3F_2\{-23/6, 11/6, 1/6; -4/3, 1;[2\beta(\xi)]^{-2}\}}{\sqrt{\pi}\,\Gamma(17/6)\Gamma(29/6)} + \\ \dfrac{\Gamma(-7/3){}_3F_2\{-3/2, 1/2, 5/2; 10/3, 10/3;[2\beta(\xi)]^{-2}\}}{2^{14/3}\pi\,\Gamma(10/3)\,[\beta(\xi)]^{14/3}} - \\ \dfrac{\Gamma(7/6)\Gamma(4/3){}_3F_2\{-17/6, -5/6, 7/6; -1/3, 3;[2\beta(\xi)]^{-2}\}}{2^3\sqrt{\pi}\,\Gamma(11/6)\Gamma(23/6)[\beta(\xi)]^2} - \\ \dfrac{\Gamma(-4/3){}_3F_2\{-3/2, 1/2, 5/2; 7/3, 13/3;[2\beta(\xi)]^{-2}\}}{2^{14/3}\pi\,\Gamma(13/3)\,[\beta(\xi)]^{14/3}} \end{bmatrix}$$

Using Eq. (12), Eq. (13), and Eq. (14), $W_c(\xi)$ is calculated with $\gamma=d/D$, $\mu=0$, and $W_p(\xi)$ is calculated with $\gamma=d/D$, $\mu=b/D$.

Having obtained a theoretical expression for $\sigma_\delta^2$ in terms of a weighted integral of $C_n^2$ we may now consider the relation between $\sigma_\delta^2$ and $\sigma_\chi^2$. Eq. (1) may be written in a normalized form as follows:

$$\sigma_\chi^2 = 0.1242\left(\frac{2\pi}{\lambda}\right)^{7/6} L^{11/6} \int_0^1 d\xi\, C_n^2(\xi L) w_\chi(\xi) \quad (15)$$

where $w_\chi(\xi)$ is the normalized weighting function given by:

$$w_\chi(\xi) = \frac{[\xi(1-\xi)]^{5/6}}{\int_0^1 d\xi[\xi(1-\xi)]^{5/6}} \quad (16)$$

$$= (0.2205)^{-1}[\xi(1-\xi)]^{5/6}.$$

Considering the form of Eq. (10) and Eq. (15), we see that both $\sigma_\delta^2$ and $\sigma_\chi^2$ are proportional to a weighted integral of $C_n^2(z)$. Thus, if there exists an optical configuration for which $w_\delta(\xi) \cong w_\chi(\xi)$, then for any turbulence profile $C_n(Z).$) it follows that:

$$\int_0^1 d\xi\, C_n^2(\xi L) w_\chi(\xi) \cong \int_0^1 d\xi\, C_n^2(\xi L) w_\delta(\xi) \quad (17)$$

$$\sigma_\chi^2 \left[0.1242\left(\frac{2\pi}{\lambda}\right)^{7/6} L^{11/6}\right]^{-1} \cong \sigma_\delta^2 \left[\frac{128\sqrt{3}\,\Gamma(8/3)}{\pi^2}\left(\frac{2\pi}{\lambda}\right)^2 D^{5/3} L W_{0\delta}\right]^{-1}$$

$$\sigma_\chi^2 \cong \left[\frac{0.1242\pi^2}{128\sqrt{3}\,\Gamma(8/3)(2\pi)^{5/6} W_{0\delta}}\right] F_D^{-5/6} \sigma_\delta^2$$

Eq. (17) is the relationship used in Eq. (7) to estimate the Rytov parameter from $\sigma_\delta^2$.

The accuracy of the DDTV Rytov parameter estimation method described above depends upon finding an optical configuration for which $w_\delta(\xi) \cong w_\chi(\xi)$. The normalized weighting function $w_\chi(\xi)$ for the Rytov parameter shown in Eq. (16) is symmetric about $\xi=0.5$ and is zero at both ends of the propagation path. The optical configuration used for the Rytov parameter monitor should lead to a weighting function for $\sigma_\delta^2$ with similar properties. Differential-tilt variance is always zero-weighted at the source. For spatially separated apertures, however, differential-tilt variance will have a maximum weighting at the aperture plane. Taking the difference of the differential-tilt variance for the non-converging and converging geometries with the same aperture separation removes the weighting at the aperture plane. Thus, all configurations of the DDTV apparatus will lead to a weighting function that is zero on both ends and reaches a maximum at some point along the path. Placing the apertures closer together pulls the peak of the weighting function closer to the aperture plane. Likewise, moving the sources closer together pushes the peak of the weighting function closer to the source plane.

Through empirical studies, we have found many configurations for which the fit between $w_\delta(\xi)$ and $w_\chi(\xi)$ is good. There are, however, a few considerations that may be used to guide our choice among these many options. First, Eq. (17) indicates that for a given Rytov, $\sigma_\delta^2$ is proportional to $F_D^{5/6}$. Thus, for increased sensitivity, we wish to make the Fresnel number of our apertures as large as possible. Since our apertures are likely to be sub-apertures of a larger pupil, then the largest attainable non-overlapping apertures would be separated by d/D=1. If over-lapping apertures can be attained in the pupil, then the Fresnel number may be increased. Small separations will also reduce sensitivity to outer scale effects, in which case the infinite outer scale analysis we have performed remains valid. If the separations are too small, however, sensitivity will degrade as $\sigma_\delta^2$ becomes smaller and smaller.

Figure 3A:
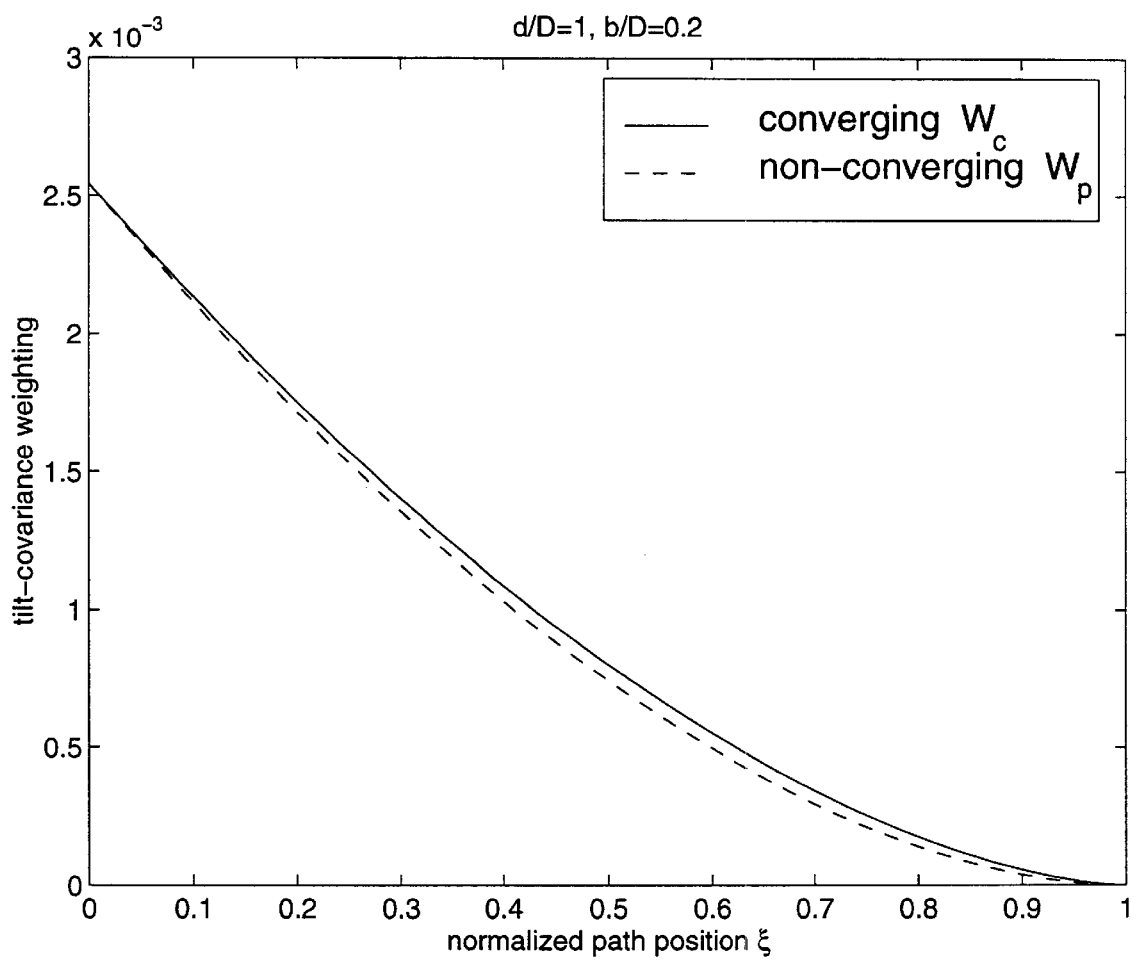
FIG. 3(*a*) shows the path weighting functions for tilt covariance associated with the converging and non-converging propagation geometries.
Figure 3B:
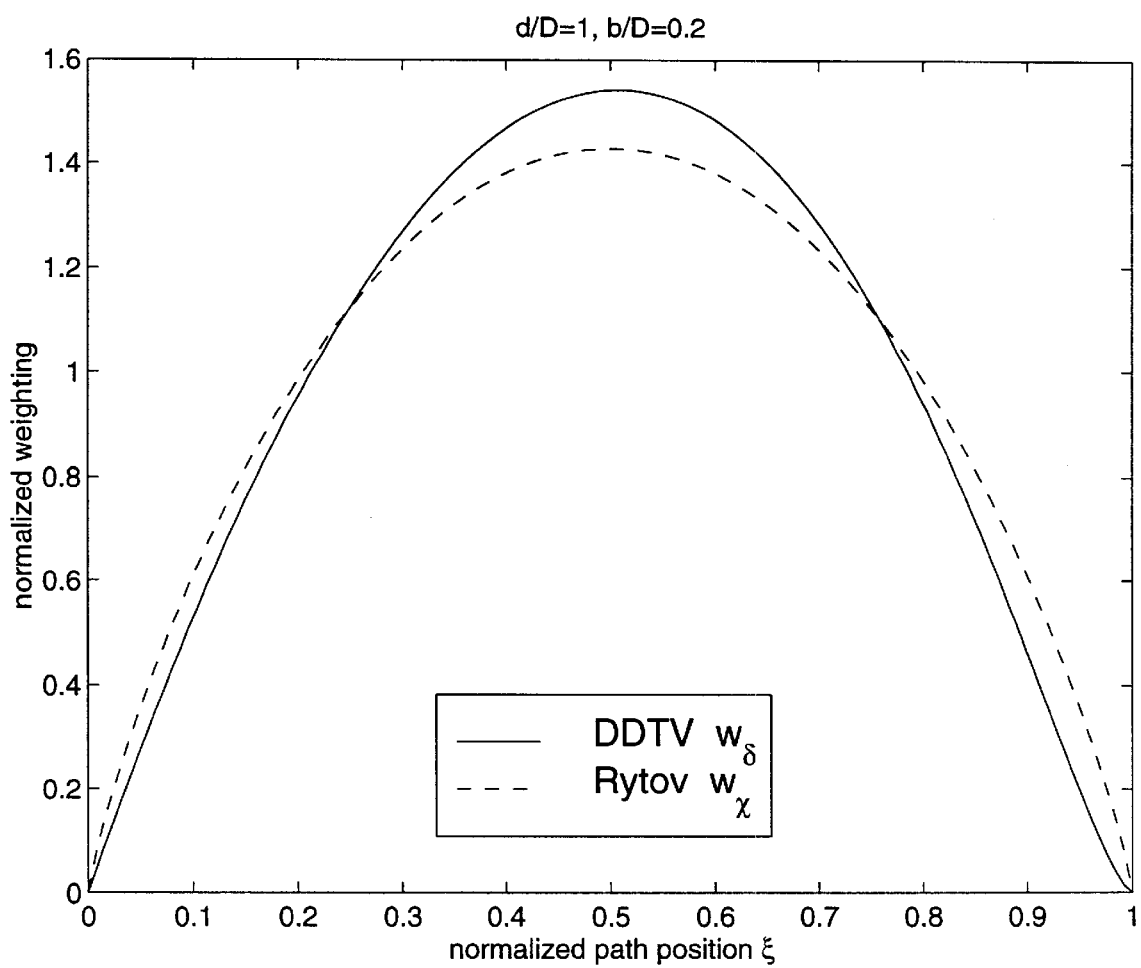

The considerations mentioned above have lead us to consider an optical configuration for which the aperture separation is d/D=1 and the source separation is b/D=0.2. The choice of b/D=0.2 follows from the selection of d/D=1 and considering the form of $w_\delta$ for various values of b. FIG. 3(a) shows the various weighting functions arising from d/D=1, b/D=0.2. FIG. 3(a) shows the (non-normalized) weighting functions for the tilt covariance associated with the converging and non-converging geometries. Recall from Eq. (11) that $w_\delta(\xi)$ is proportional to the difference of these two weighting functions. The normalized weighting function $w_\delta(\xi)$ is shown in FIG. 3(b). For comparison, $w_\chi(\xi)$ is plotted with $w_\delta(\xi)$. FIG. 3(b) illustrates that for dD=1, b/D=0.2, $w_\delta(\xi)$ and $w_\chi(\xi)$ are in good agreement over the entire propagation path.

To assess the impact of the small differences between $w_\delta(\xi)$ and $w_\chi(\xi)$ noted in FIG. 3(b) on the DDTV technique, we take Eq. (17) to represent an estimator for the Rytov parameter, designated $\hat{\sigma}_\chi^2$.

$$\hat{\sigma}_\chi^2 \equiv \left[ \frac{0.1242 \pi^2}{128 \sqrt{3} \, \Gamma(8/3)(2\pi)^{5/6} W_{0\delta}} \right] F_D^{5/6} \sigma_\delta^2 \quad (18)$$

$$= 0.1242 \left( \frac{2\pi}{\lambda} \right)^{7/6} L^{11/6} \int_0^1 d\xi C_n^2(\xi L) w_\delta(\xi).$$

Notice that the last line of Eq. (18) is similar to Eq. (15), where $w_\chi(\xi)$ has been replaced by $w_\delta(\xi)$ in the integral over the propagation path. Using the definition for $\hat{\sigma}_\chi^2$ in Eq. (18) and Eq. (15) for $\sigma_\chi^2$ the relative error $\epsilon$ in the Rytov parameter estimator is given by:

$$\varepsilon = \left| \frac{\hat{\sigma}_\chi^2 - \sigma_\chi^2}{\sigma_\chi^2} \right| \quad (19)$$

$$= \left| \frac{\int_0^1 d\xi C_n^2(\xi L) w_\delta(\xi)}{\int_0^1 d\xi C_n^2(\xi L) w_\chi(\xi)} - 1 \right|.$$

Thus, the value of $\epsilon$ depends upon the particular realization of $C_n^2(z)$ encountered when measuring $\sigma_\delta^2$.

To quantity the relative error in the DDTV estimator of the Rytov parameter considering variations in the turbulence profile, we generated random $C_n^2$ values over the propagation path using a Gaussian random number generator. Notice in Eq. (19) that $\epsilon$ is independent of any constant multiplier of $C_n^2$. That is, if $C_n^2(\xi L) = C_0 \rho(\xi)$, then $\epsilon$ is given by:

$$\varepsilon = \left| \frac{\int_0^1 d\xi \rho(\xi) w_\delta(\xi)}{d\xi \rho(\xi) w_x(\xi)} - 1 \right|. \quad (20)$$

Figure 4:
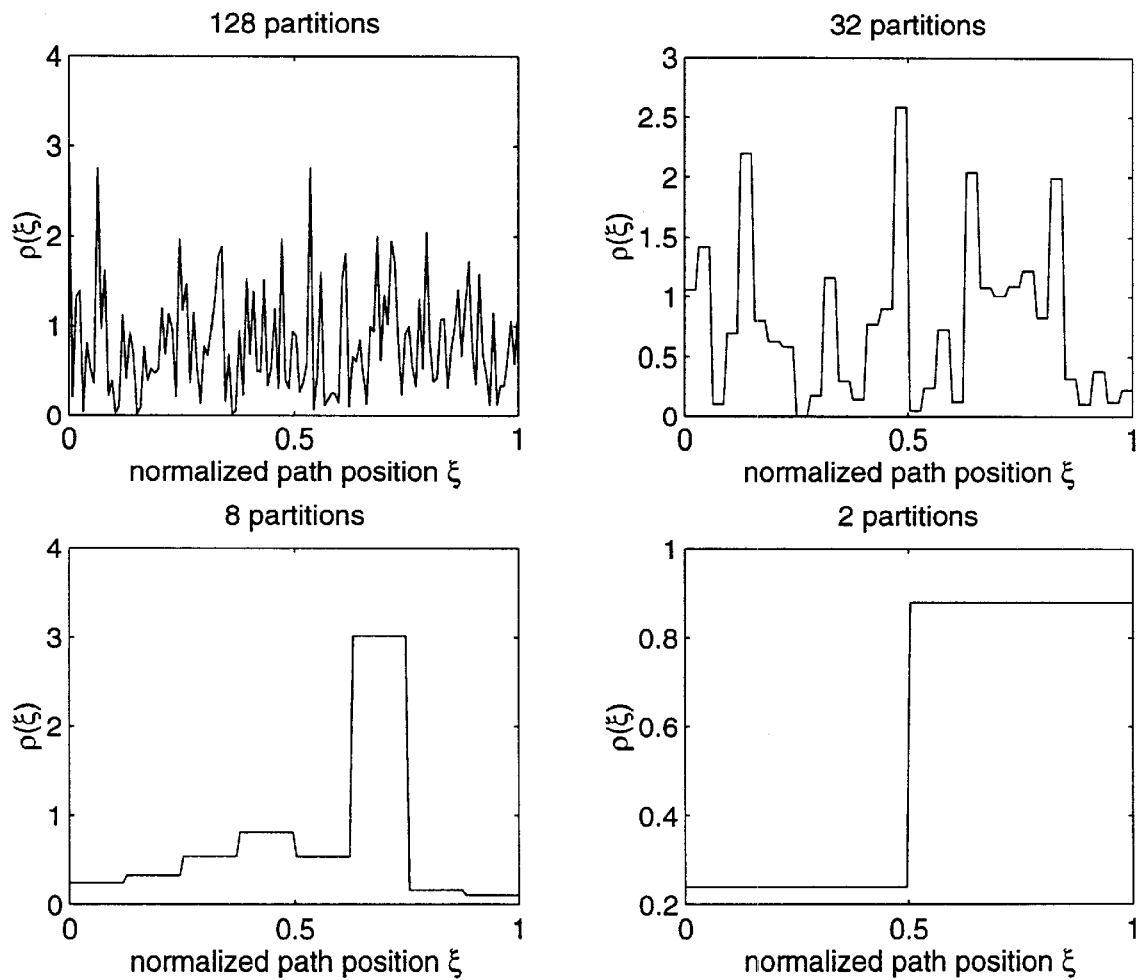
FIG. 4 shows realizations of turbulence profiles generated to quantify the relative error of the DDTV Rytov parameter estimation technique.
Figure 5:
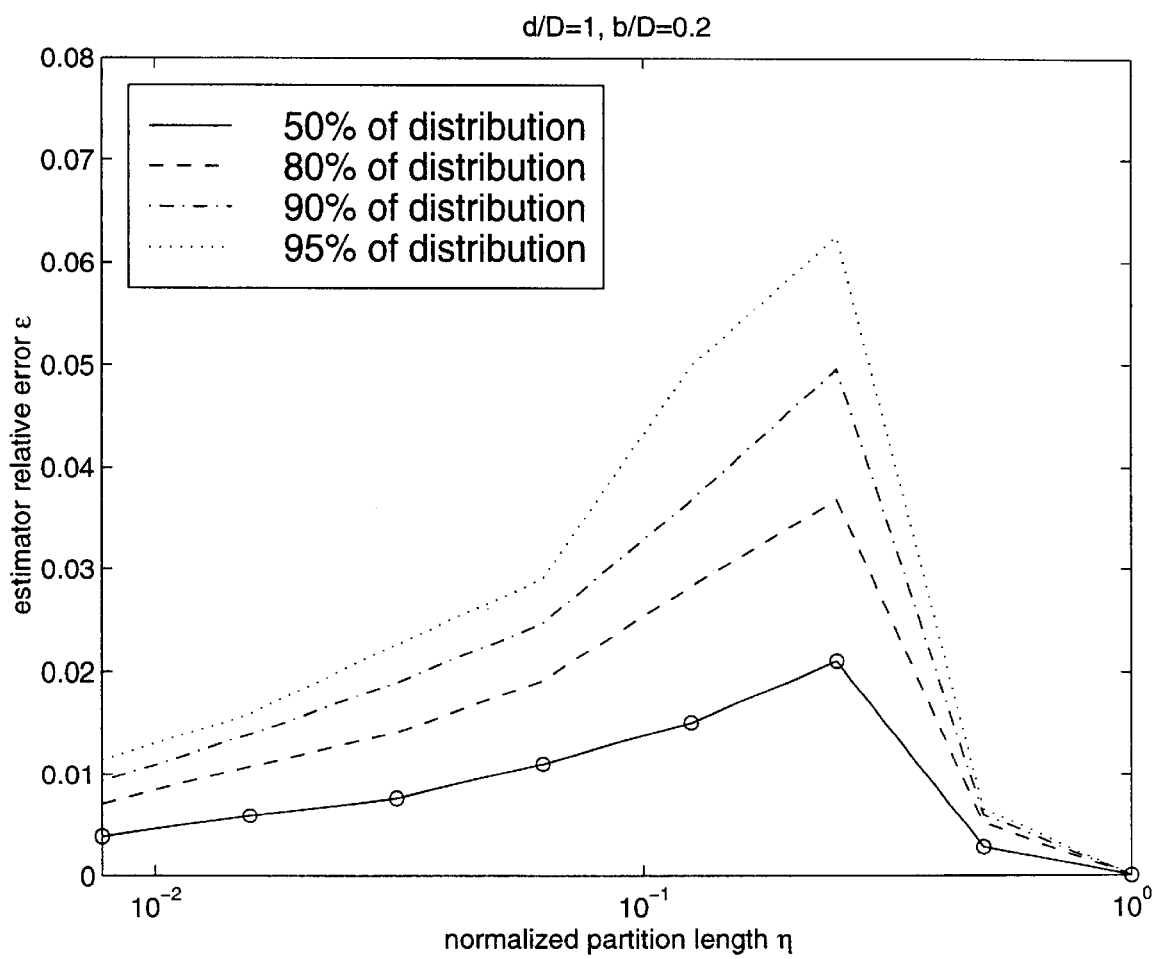
FIG. 5 is a plot of the relative error of the DDTV Rytov parameter estimation technique for varying partition size, normalized to path length.

Values of $\rho(\xi)$ were generated by taking the absolute value of Gaussian random numbers with zero mean and unit variance. Additionally, we altered the scale size of the turbulence strength variations by varying the number of constant $\rho(\xi)$ partitions (layers) contained within the propagation path. The number of turbulence partitions within the path was varied from 128 down to 1 by a factor of 2. Example realizations of the normalized turbulence profile $\rho(\xi)$ for varying partitioning of the propagation path are shown in FIG. 4. For each partitioning size, 1000 random realizations of $\rho(\xi)$ were produced. For each random profile, the relative error was computed according to Eq. (20). From these random relative errors, the relative error corresponding to 50%, 80%, 90% and 95% of the distribution were determined. These results are shown in FIG. 5 as a function of the partition size normalized to the path length, i.e., $\eta = 1/128, 1/64, 1/32, \ldots, 1/1$.

Notice that the relative error peaks near $\eta=0.25$. At this maximum, more than 95% of the random relative error values are below 0.07, 80% are below 0.04 and approximately 50% are below 0.02. Thus, the small errors noticed in FIG. 3(b) have a minimal impact on the relative error of the Rytov parameter estimate. It is interesting to note that for a uniform turbulence profile ($\eta=1$), the relative error is identically zero. This can be deduced by considering Eq. (20), where $\rho(\xi)$ is set to a constant value. In this case, the integral of each weighting function over the path is 1, giving $\epsilon=0$. This is indicative of the fact that if the turbulence profile is truly uniform, then any turbulence statistic may be used to calculate $C_n^2$, which in turn may be used to calculate the Rytov parameter. In general, we may not assume turbulence-strength uniformity across the path and therefore $\epsilon>0$.

In addition to estimator error, we must also consider estimator sensitivity. Generally, we wish $\sigma_\delta^2$ to be as large as possible without compromising the small relative errors shown in FIG. 5. As indicated in Eq. (17), the magnitude of $\sigma_\delta^2$ at a given Rytov parameter depends upon the Fresnel number of the optical system. From Eq. (17), we may write the normalized DDTV quantity $\sigma_\delta^2 F_D^{-5/6}$ as:

$$\sigma_\delta^2 F_D^{-5/6} = \frac{128\sqrt{3}\,\Gamma(8/3)(2\pi)^{5/6}}{0.1242\pi^2} W_{0\delta}\sigma_\chi^2. \quad (21)$$

Figure 6A:
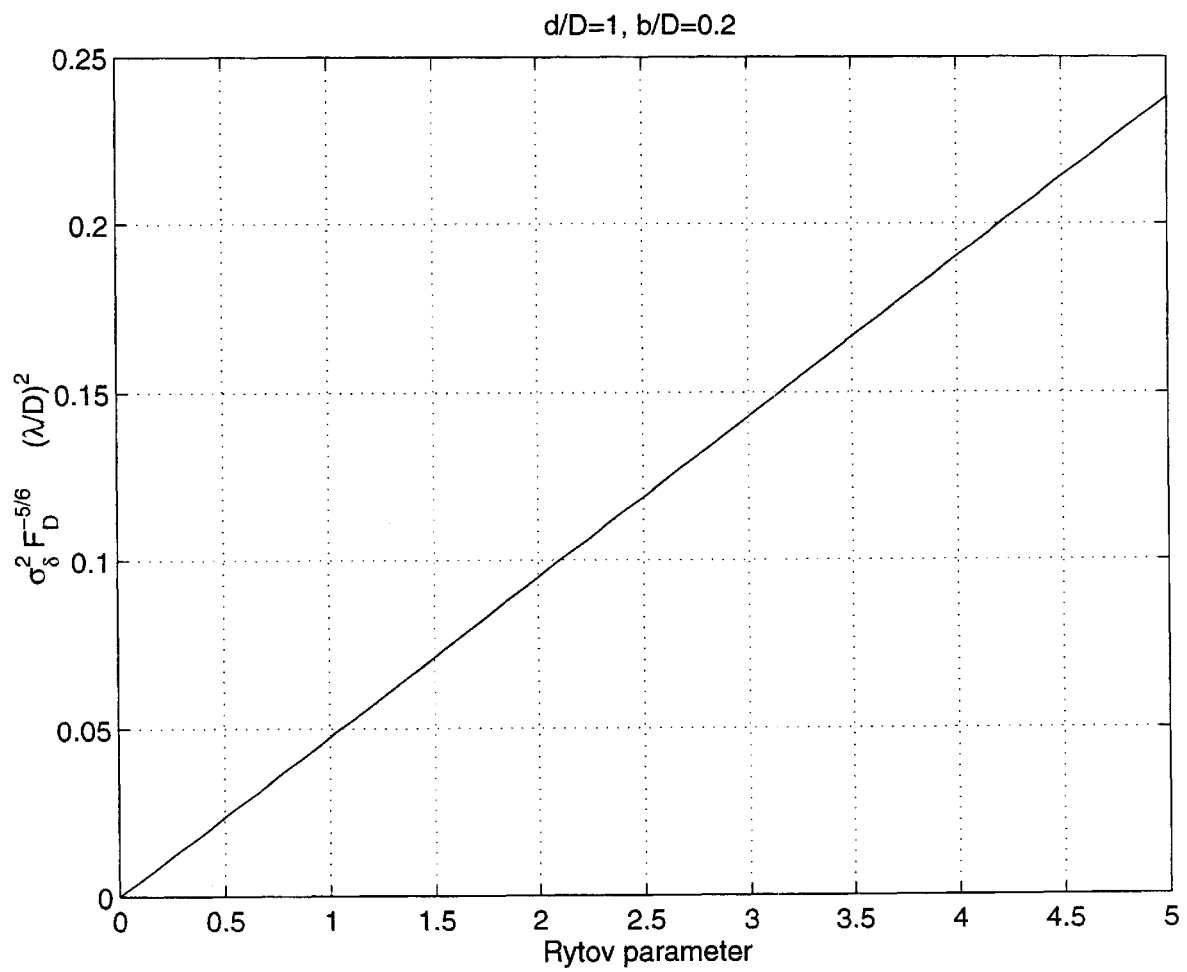
FIG. 6(*a*) is a plot of the normalized DDTV quantity $\sigma_\delta^2 F_D^{-5/6}$ for a range of Rytov parameters.
Figure 6B:
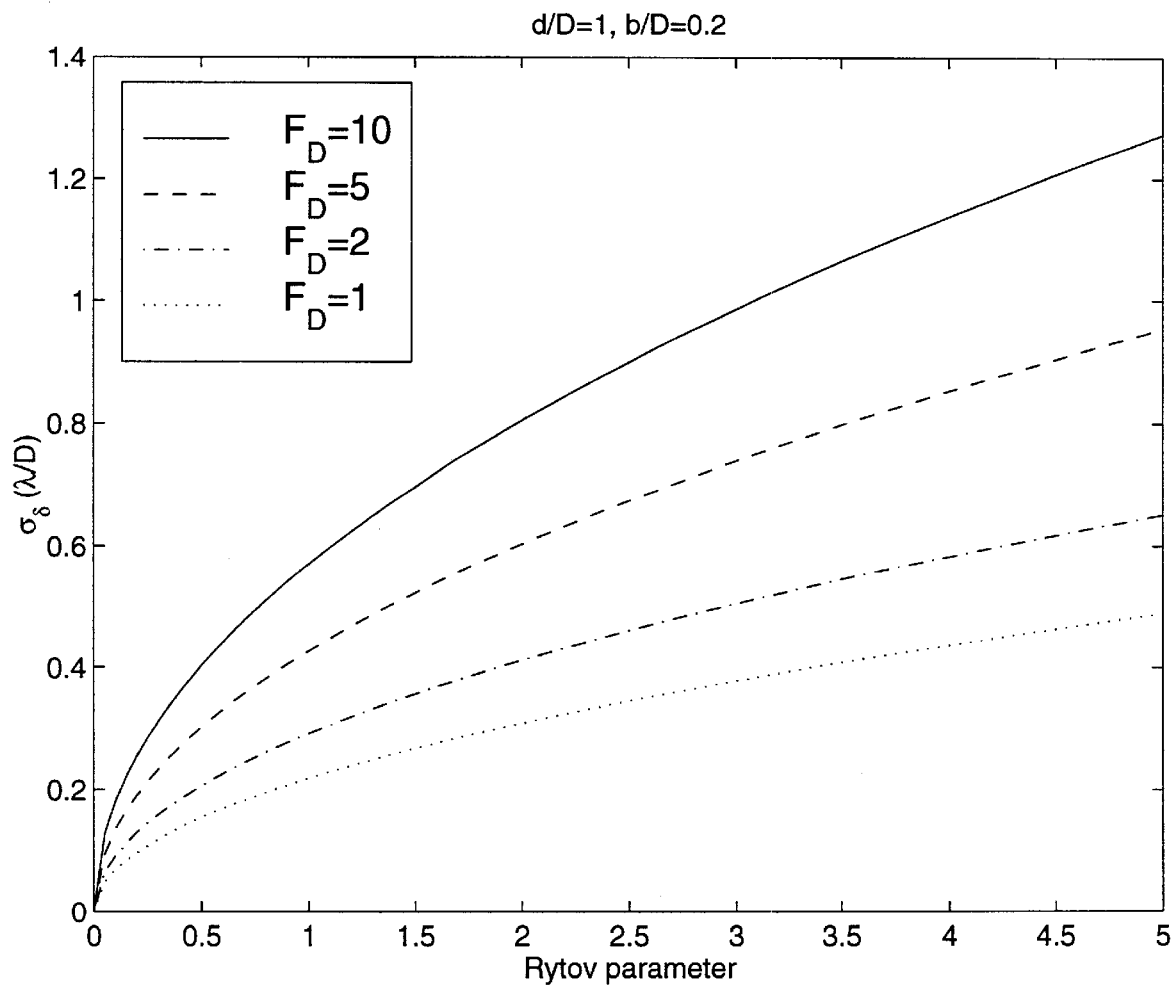

Since this normalized quantity depends only upon d/D and b/D, then $\sigma_\delta$ may be increased by increasing the system Fresnel number while maintaining a constant relative error. FIG. 6 shows a plot of both the normalized DDTV quantity a $\sigma_\delta^2 F_D^{-5/6}$ and the value (in units of $\lambda$/D) of $\sigma_\delta$ for several Fresnel numbers as a function of Rytov. All results are for d/D=1 and b/D=0.2. These plots illustrate that for the optical configuration considered, the equivalent jitter to be measured is a reasonable fraction of $\lambda$/D. For instance, with $F_D$=5, $\sigma_\delta \cong 0.4\,\lambda$/D when $\sigma_\chi^2 \cong 1$.

Various devices have been invented previously that provide characterization parameters for atmospheric turbulence (U.S. Pat. Nos. 5,150,171, 5,303,024, 5,796,105, and 5,343,287). None of these devices provide a direct method for estimating the Rytov parameter as defined in Eq. (1). In cases where little is known about the distribution of turbulence over the propagation path, estimating the Rytov parameter from observable quantities using any of these devices requires making questionable assumptions about $C_n^2(z)$. Typically, the turbulence strength is assumed to be uniform or to follow some standard model throughout the propagation volume, and the measured irradiance variance is used to infer the Rytov parameter through a curve fit to experimental and simulated data. This approach is taken due to the inaccuracy of Rytov theory in the saturation regime for scintillation, and may lead to large errors in the estimated Rytov parameter when modeling assumptions are violated.

To address the fundamental limitations of current atmospheric metrology systems, we have developed the instrumentation and processing required for a Rytov parameter monitor. This system and related techniques use a measurement of the difference of differential-tilt variance (DDTV) $\sigma_\delta^2$ obtained with an optical apparatus configured such that the Rytov parameter is proportional to $\sigma_\delta^2$. The constant of proportionality is determined by theoretical analysis. No a priori assumptions are made about the turbulence profile, and no simulation-based modeling is required. Studies indicate that the relative error of this method is approximately 5% in the worst cases. The analysis shows that the equivalent jitter for this method is on the order of 0.1 $\lambda$/D, a figure easily obtained with most electronic cameras and reasonable aperture sizes. The DDTV method described here is also insensitive to errors from gimbal motion and any additive noise sources. Furthermore, the method is thought to be insensitive to outer scale effects and immune to saturation phenomena typically experienced with irradiance-based methods in strong turbulence.

The basic instrumentation requires two spatially separated point-source beacons of distinct wavelength and three electronic cameras forming images from two spatially separated apertures. One alternative configuration is proposed which uses two spatially separated point-source beacons of the same wavelength pulsed successively with a short delay, forming images on two cameras from two spatially separated apertures. A final alternative configuration is proposed which requires only one point-source beacon and two cameras forming images from two spatially separated apertures. Novel processing algorithms are employed in the single-source alternative to arrive at an estimate of the Rytov parameter.

Apart from the basic apparatus shown in FIG. 1 and processing previously outlined, there are at least two alternative modes in which this type of system may operate. Each alternative is justified in terms of the theory of operation described.

The differential-tilt Rytov parameter monitor described requires two point sources operating at distinct wavelengths and a total of three cameras to record image data associated with two apertures. The basic system relies upon spectral bandpass filters for source discrimination to give measurements for the converging and non-converging propagation geometries. The quality of the bandpass filters will ultimately place limitations upon how closely spaced the two sources may be in wavelength. To avoid errors that may be introduced by the spectral diversity of the two sources, it may be advantageous to discriminate between the beacons temporally, with the temporal separation between the beacon signals being short enough to "freeze" the atmosphere. This is the basic approach used in the time-duplex differential-tilt Rytov parameter monitor.

Figure 7:
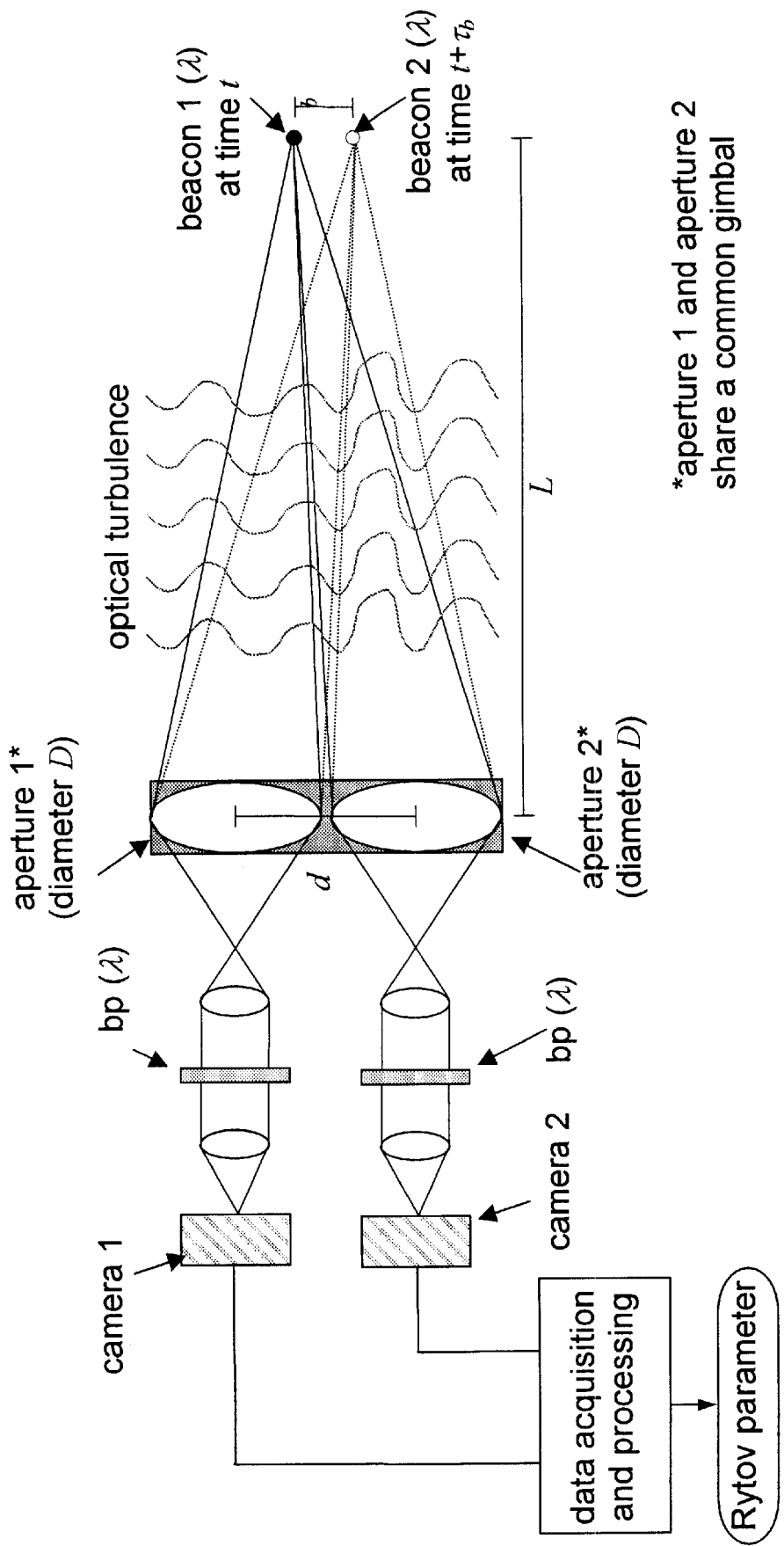
FIG. 7 is a schematic for a time-duplex alternative apparatus for the differential-tilt Rytov parameter monitor.

The system configuration for the time-duplex version of the Rytov parameter monitor is shown in FIG. 7. In this configuration, beacon 1 pulses at time t. A single camera image associated with each aperture at time t is acquired. These images are then processed to yield the centroid data $d_1(t)$ and $d_2(t)$. Beacon 2 then pulses at time $t+\tau_b$, resulting in the centroid data $d_1(t+\tau_b)$ and $d_2(t+\tau_b)$. The temporal separation period $\tau_b$ must be short enough so that the atmosphere does not change between the two pulses. As a general guideline, $\tau_b$ should be chosen such that $$\frac{v\tau_b}{D} \le 0.1.$$

The exposure times for the cameras should not change from the basic design. For v=10 m/s and D=0.1 m, the beacons would be separated by 1 millisecond, and the camera exposure would be 100 microseconds.

Combinations of the acquired tilt data $d_1(t), d_2(t), d_1(t+\tau_b)$ and $d_2(t+\tau_b)$ are then taken to represent the converging and non-converging propagation geometries. In this approach the sets $d_1(t), d_2(t),$ and $d_1(t+\tau_b), d_2(t+\tau_b)$ each give the converging geometry. The set $d_1(t), d_2(t+\tau_b)$ gives the non-converging geometry. With these signals, $\sigma_\delta^2$ may be computed as:

$$\sigma_\delta^2 = \langle [d_1(t) - \langle d_1(t)\rangle - d_2(t+\tau_b) + \langle d_2(t+\tau_b)\rangle]^2\rangle - \langle [d_1(t) - \langle d_1(t)\rangle - d_2(t) + \langle d_2(t)\rangle]^2\rangle \quad (22)$$

Alternatively, $\sigma_\delta^2$ may also be computed as:

$$\sigma_\delta^2 = \langle [d_1(t) - \langle d_1(t)\rangle - d2(t+\tau_b) + \langle d2(t+\tau_b)\rangle]^2\rangle - \langle [d_1(t+\tau_b) - \langle d_1(t+\tau_b)\rangle - d2(t+\tau_b) + \langle d2(t+\tau_b)\rangle]^2\rangle \quad (23)$$

In practice, it may be useful to compute $\sigma_\delta^2$ by the methods indicated in both Eq. (22) and Eq. (23). In either case, the Rytov parameter is estimated from $\sigma_\delta^2$ according to Eq. (7).

The principle advantage to the time-duplex alternative to the basic design is that because the beacons are separated temporally, the bandpass filters used in the system can be of lower quality. Additionally, only two cameras are used in this alternative as compared to three cameras in the basic design. The disadvantage to this alternative is that the beacons must be pulsed, and the camera exposures must be synced to the pulsing of the beacons. It is not anticipated that the beacons and cameras must be synced to an external reference, but only that each camera syncs its exposure to each pulse.

Both the basic system shown in FIG. 1 and the time-duplex alternative shown in FIG. 7 require two point sources to estimate the Rytov parameter. When propagating on a ground-based range, these systems may be practical. When working with astronomical sources, however, finding two beacons with the correct spatial separation may be difficult. In this case, a single-source alternative system is desirable. The limitations of employing a single beacon may be partially overcome by more sophisticated data processing.

Figure 8:
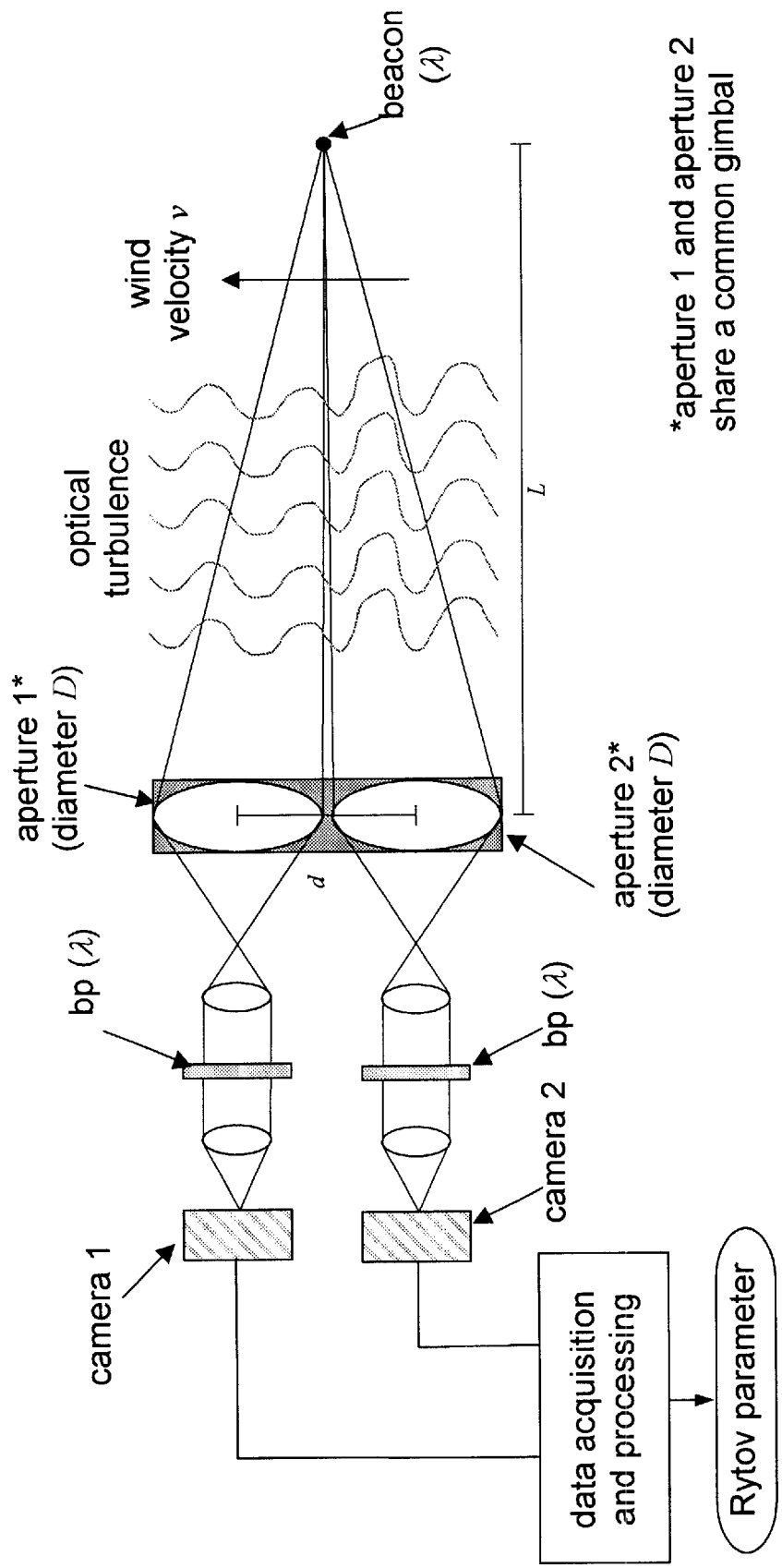
FIG. 8 is a schematic for a single-source alternative apparatus for the differential-tilt Rytov parameter monitor.

The optical apparatus for a single-source differential-tilt Rytov parameter monitor is shown in FIG. 8. In this system, a single point source is observed in cameras associated with each of the common-gimbal apertures. This system is essentially the same apparatus used in systems which measure the transverse coherence length $r_0$ (F. D. Eaton, et al., "Phase structure function measurements with multiple apertures," in *Proc. SPIE: Propagation Engineering,* vol. 1115, pp. 218–223, 1989). The bandpass filters used in this system are for filtering a particular range of wavelengths only, and not for beacon discrimination. Processing each of the camera images results in two tilt data signals $d_1(t)$ and $d_2(t)$. The differential tilt variance between these two signals is the variance for the converging geometry. Obtaining the variance for the non-converging geometry requires further processing.

To obtain the differential tilt variance for a non-converging propagation geometry, we rely on the frozen-flow nature of atmospheric turbulence. Under these assumptions, a time delay may be equated to a spatial offset. The first step in applying time-delayed data is to establish which of the two apertures is "downstream" in the flow of turbulence, i.e., the tilt signal that is a time-delayed version of the other. To establish the downstream tilt signal, we consider the temporal cross-correlation of $d_1(t)$ and $d_2(t)$ as follows:

$$R(\tau) = \frac{\langle (d_1(t+\tau) d_2(t) \rangle}{\sqrt{\langle d_1^2(t) \rangle \langle d_2^2(t) \rangle}} \qquad (24)$$

If the cross-correlation peaks at a positive value of $\tau$, then the downstream signal $d_{down}(t) = d_1(t)$. If the cross-correlation peaks at a negative value of $\tau$ then signal $d_{down}(t) = d_2(t)$. If the magnitude of the time delay $\tau_m$ for which the cross-correlation is a maximum is applied to the downstream signal, then under frozen flow we assume that this time adjustment shifts the entire propagation path in the upstream direction. Using the method outlined above for determining the downstream tilt signal, $\sigma_\delta^2$ may then be computed as:

$$\sigma_\delta^2 = \langle [d_{down}(t) - d_{down}(t-\tau_m)]^2 \rangle - \langle [d_1(t) - \langle d_1(t) \rangle - d_2(t) + \langle d_2(t) \rangle]^2 \rangle. \qquad (25)$$

With this value of $\sigma_\delta^2$ the Rytov parameter may then be computed according to Eq. (7). For this system, however, the value of $W_{0\delta}$ must be computed from Eq. (12), Eq. (13), and Eq. (14), with $\gamma = d/D$, $\mu = 0$ for the converging geometry and $\gamma = d/D$, $\mu = d/D$ for the non-converging geometry.

Figure 9A:
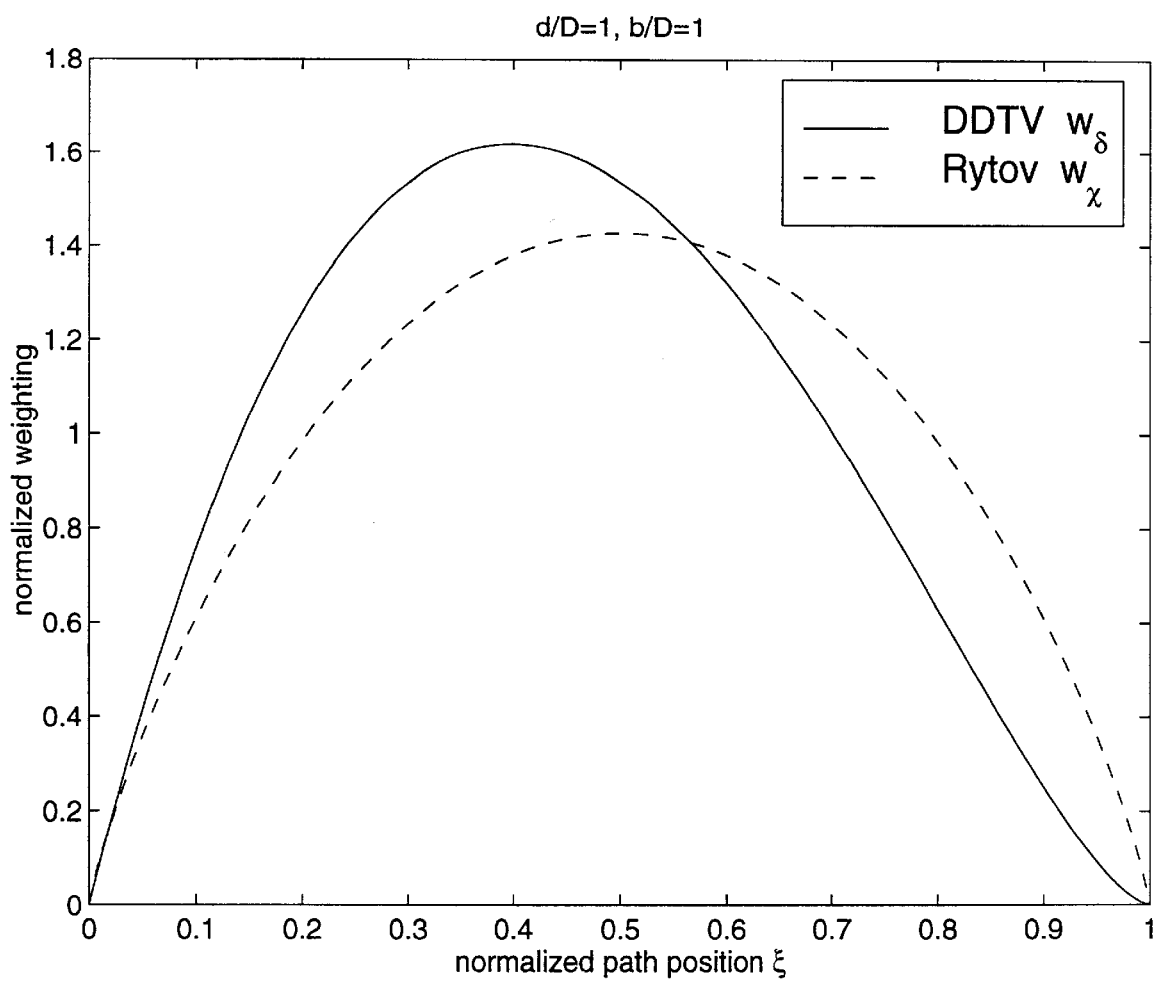
FIG. 9(*a*) is a plot of the normalized weighting function for $\sigma_\delta^2$ for $d/D=1$ and $b/D=1$ with the normalized weighting function for the Rytov parameter shown as a reference.
Figure 9B:
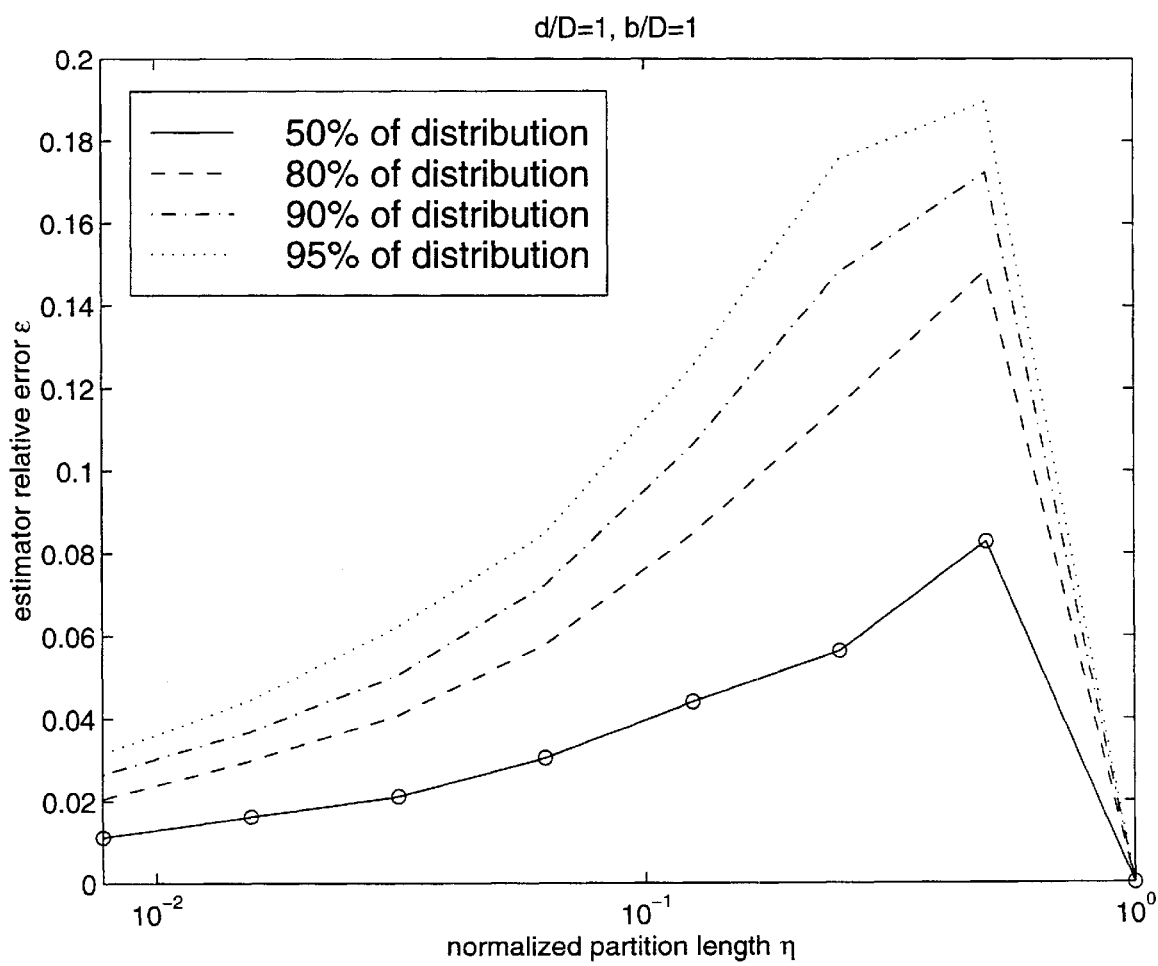

The clear advantage of this alternative over the basic or time-duplex system is that a single beacon may be employed. Also, the system requirements are the same as for a conventional $r_0$ monitoring device. In fact, depending upon the specifications of the hardware, the processing outlined in this subsection may be applied to an $r_0$ monitoring device to develop a Rytov parameter monitor. The major disadvantage to this alternative system is its reliance on the validity of frozen-flow turbulence, which may not generally hold depending upon the wind velocity and turbulence strength. Additionally, even when frozen-flow assumptions are valid, this alternative processing results in a non-converging propagation configuration where the beacon separation is the same as the aperture separation. FIG. 9(a) shows the effect on the weighting function of $\sigma_\delta^2$ when $d/D = b/D = 1$. Due to the errors in path weighting between at $\sigma_\delta^2$ and $\sigma_\chi^2$ the relative error in the Rytov parameter estimate increases significantly as shown in FIG. 9(b). Relative errors in the Rytov estimate are approximately 15% for the single-source alternative system as compared to 5% relative error for the basic system.

I claim:

1. A differential-tilt Rytov parameter monitor for estimating the value of the theoretical expression for the Rytov parameter for point source propagation of light through atmospheric optical turbulence, said monitor comprised of:
    a. a first point source light beacon at a first wavelength;
    b. a second point source light beacon at a second wavelength spatially separated from said first beacon;
    c. a first and a second aperture of the same diameter located in a plane and separated by a short distance in the same direction as the point source beacons are separated from each other and at a distance L from said beacons;
    d. a first bandpass filter at the center wavelength of said first beacon;
    e. a first camera positioned so as to receive the light from said first beacon, after passing through said first aperture and said first bandpass filter;
    f. a beamsplitter;
    g. a second bandpass filter at the center wavelength of said second beacon;
    h. a second camera positioned so as to receive the light from said second beacon after passing through said second aperture, said beamsplitter, and said second bandpass filter;
    i. a second first bandpass filter at the center wavelength of said first beacon;
    j. a third camera positioned so as to receive the light from said first beacon after passing through said second aperture, being reflected by said beamsplitter, and passing through said second first bandpass filter; and
    k. computer means for estimating the value of the theoretical expression for the Rytov parameter based on the inputs of said first, second, and third cameras using the difference of differential-tilt variance (DDTV) technique.

2. The differential-tilt Rytov parameter monitor of claim 1, whereby the wavelength separation of said first beacon and said second beacon is the smallest amount that permits proper rejection by said bandpass filters centered at said first and second wavelengths.

3. A time-duplex differential-tilt Rytov parameter monitor for estimating the value of the theoretical expression for the Rytov parameter for point source propagation of light through atmospheric optical turbulence, said monitor comprised of:
    a. a first pulsing point source light beacon at a wavelength $\lambda$;
    b. a second pulsing point source light beacon at a wavelength $\lambda$ spatially separated from said first beacon and alternately pulsing with said first beacon, the time between said first beacon pulse and said second beacon pulse being short enough such that the atmosphere does not change between the two pulses;
    c. a first and a second aperture of the same diameter located in a plane and separated by a short distance in the same direction as the point source beacons are separated from each other and at a distance L from said beacons;

d. a first bandpass filter centered at wavelength $\lambda$;

e. a first camera positioned so as to receive the light alternately from either said first or second beacon, after passing through said first aperture and said first bandpass filter;

f. a second bandpass filter centered at wavelength $\lambda$;

g. a second camera positioned so as to receive the light alternately from either said first or second beacon, after passing through said second aperture and said second bandpass filter; and h. computer means for estimating the value of the theoretical expression for the Rytov parameter based on the inputs of said first and second cameras using the difference of differential-tilt variance (DDTV) technique accounting for the time-alternating inputs.

4. A single-source differential-tilt Rytov parameter monitor for estimating the value of the theoretical expression for the Rytov parameter for point source propagation of light through atmospheric optical turbulence, said monitor comprised of:

a. a point source light beacon at a wavelength $\lambda$;

b. a first and a second aperture of the same diameter located in a plane and separated by a short distance from each other and at a distance L from said beacon;

c. a first bandpass filter centered at wavelength $\lambda$;

d. a first camera positioned so as to receive the light from said beacon, after passing through said first aperture and said first bandpass filter;

e. a second bandpass filter centered at wavelength $\lambda$;

f. a second camera positioned so as to receive the light from said beacon, after passing through said second aperture and said second bandpass filter; and g. computer means for estimating the value of the theoretical expression for the Rytov parameter based on the inputs of said first and second cameras using the assumption that a time delay may be equated to a spatial offset.

* * * * *